United States Patent [19]

Pellico

[11] 4,161,410

[45] Jul. 17, 1979

[54] SETTABLE DENTAL COMPOSITIONS WITH POLYTERPENE BINDER

[75] Inventor: Michael A. Pellico, Los Angeles, Calif.

[73] Assignee: Denton Industries, Inc., Los Angeles, Calif.

[21] Appl. No.: 908,241

[22] Filed: May 22, 1978

Related U.S. Application Data

[63] Continuation-in-part of Ser. No. 736,241, Oct. 27, 1976, abandoned.

[51] Int. Cl.$^2$ ................................................ C09K 3/00
[52] U.S. Cl. .......................................... 106/35; 32/15; 106/219; 106/237; 106/243; 260/18 R
[58] Field of Search ................ 106/35, 219, 237, 243; 260/28 R; 32/15

[56] References Cited

U.S. PATENT DOCUMENTS

| | | | |
|---|---|---|---|
| 3,376,134 | 4/1968 | Stahly et al. | 260/407 |
| 3,837,865 | 9/1974 | Pellico | 106/35 |
| 3,859,107 | 1/1975 | Garcia | 106/219 |
| 3,944,123 | 3/1976 | Jacobs | 106/219 |

FOREIGN PATENT DOCUMENTS 700633  12/1964  Canada .................................... 106/35

*Primary Examiner*—Lorenzo B. Hayes
*Attorney, Agent, or Firm*—Donald Diamond

[57] ABSTRACT

An oral, settable dental composition is prepared by interacting Component A containing (i) a liquid polycarboxylic acid such as $C_{36}$ dimer acid, (ii) a reaction rate activator exemplified by acetic acid, zinc acetate, ethanol, phenylmethanol or mixtures thereof and (iii) a thermoplastic hydrocarbon resin as, for example, polyterpene resin with Component B containing a metallic base such as zinc oxide or a mixture of zinc oxide and magnesium oxide in a suitable fluid carrier.

16 Claims, No Drawings

4,161,410

SETTABLE DENTAL COMPOSITIONS WITH POLYTERPENE BINDER

CROSS-REFERENCE TO RELATED APPLICATION

This application is a continuation-in-part of U.S. patent application Ser. No. 736,241 filed Oct. 27, 1976, now abandoned, for Settable Dental Compositions.

BACKGROUND OF THE INVENTION

This invention relates to oral, settable, dental compositions prepared by interacting a metallic base with a high molecular weight polycarboxylic acid in the presence of a reaction rate activator and a hydrocarbon binding resin.

Typically, settable dental compositions are used for taking dental impressions and, in addition, are used as pulp capping materials and as temporary cements. A settable composition is one which, after being formed, sets into a solid, cementitious, coherent mass.

In order for a settable composition to have practical utility in the dental field, it must set to a cohesive mass, following admixture of the components, within a relatively short period of time, usually not longer than about 15 minutes. Since the rate of set in the reaction of a metallic base with a high molecular weight polycarboxylic acid is too slow for dental purposes, it is necessary to include in the formulation a reaction rate activator, sometimes referred to as an accelerator, in order to increase the rate of reaction and to reduce the set time.

In addition, it has been customary in the art to include a carboxylic acid binding resin in the formulation to improve adhesiveness, impart toughness and reduce brittleness of the interacted product.

Canadian Pat. No. 700,633 (corresponding to U.S. Pat. No. 3,028,247-Molnar, 1962) discloses the use of (a) carboxylic acid resins such as modified resin and (b) reaction rate accelerators exemplified by azelaic acid, ethanol and zinc acetate in the preparation of settable dental compositions based on the interaction of a monocarboxylic fatty acid having a melting point below 65° C. with a polyvalent metallic base. The patentee emphasizes that the resin employed must possess unreacted or available carboxyl groups.

U.S. Pat. No. 3,837,865 (Pellico, 1974) discloses the preparation of settable dental compositions by interacting a polycarboxylic acid such as $C_{36}$ dimer acid with a metallic base in the presence of a carboxylic acid resin such as modified rosin and a reaction rate activator exemplified by acetic acid and zinc acetate.

SUMMARY OF THE INVENTION

In accordance with this invention, it has been discovered that hydrocarbon resins, i.e. resins which do not possess unreacted or available carboxyl groups, can be effectively used as binding resins in the preparation of settable dental compositions based on the interaction of a metallic base with reactable and solidifiable organic acids.

In one aspect of this invention, there is provided a method for preparing an oral, settable dental composition which comprises interacting:

Component A containing:
(i) a polycarboxylic acid selected from the group consisting of $C_{36}$ dimer acid, $C_{54}$ trimer acid and mixtures thereof, (ii) a reaction rate activator selected from the group consisting of lower aliphatic alcohols, lower aromatic alcohols, lower aliphatic organic acids, calcium, magnesium and zinc salts of said acids, and mixtures thereof, said reaction rate activator being present in an amount from about 1 to about 30 wt.% based on the weight of the polycarboxylic acid, provided however, that the upper weight limit of the lower aliphatic organic acids and the calcium, magnesium and zinc sales of said acids does not exceed about 10 wt.% based on the weight of the polycarboxylic acid, and (iii) polyterpene resin in an amount from about 0.3 to about 1.3 parts by weight per 1.0 part by weight of polycarboxylic acid; and Component B containing a metallic base selected from the group consisting of oxides and hydroxides of zinc, magnesium, calcium, copper and mixtures thereof, said metallic base being present in an amount from about 0.1 to about 4.0 parts by weight per 1.0 part by weight of polycarboxylic acid.

In a second aspect of this invention, there is provided a solid, coherent, cementitious, dental composition prepared by interacting Components A and B having formulations as hereinabove described.

In a third aspect of this invention, there is provided a two-component system interactable to form an oral, settable dental composition comprising Components A and B having formulations as hereinabove set forth.

DETAILED DESCRIPTION

The polycarboxylic acids which are utilized in the invention include $C_{36}$ dimer acid, $C_{54}$ trimer acid and mixtures thereof. Dimer and trimer acids are viscous liquids which are produced by the polymerization of fatty acids containing 18 carbon atoms. Dimer acid is an aliphatic, dibasic acid containing 36 carbon atoms whose structure is essentially that of a long-chain dicarboxylic acid with 2 alkyl side chains. The approximate molecular weight of $C_{36}$ dimer acid is 565. Trimer acid is an aliphatic, tribasic acid containing 54 carbon atoms whose structure is essentially that of a long-chain tricarboxylic acid with 3 or more alkyl side chains. The approximate molecular weight of $C_{54}$ trimer acid is 850. Commercially available $C_{36}$ dimer acid contains a minor amount of $C_{54}$ trimer acid and a trace amount of monobasic acid. Commercially available $C_{54}$ trimer acid contains a minor amount of $C_{36}$ dimer acid.

The metallic base which is interacted with the high molecular weight polycarboxylic acid to provide a settable dental composition is, advantageously, a polyvalent metallic base such as zinc oxide, magnesium oxide, calcium oxide, cupric oxide, zinc hydroxide, magnesium hydroxide, calcium hydroxide, cupric hydroxide and mixtures thereof. A particularly effective polyvalent metallic base is a mixture of zinc oxide and magnesium oxide.

The metallic base is generally employed in an amount from about 0.1 to about 4.0 parts by weight per 1.0 part by weight of polycarboxylic acid and, preferably, in an amount from about 0.25 to about 3.0 parts by weight per 1.0 part by weight of polycarboxylic acid.

The reaction rate activators which can be utilized in this invention are advantageously included in the polycarboxylic acid component of the two-component system in order to increase the rate of reaction between the high molecular weight organic acid and the metallic base and thereby reduce oral set time. These activators include lower aliphatic alcohols, lower aromatic alcohols, lower aliphatic organic acids, calcium, magnesium and zinc salts of such acids and mixtures thereof.

The preferred aliphatic alcohols are saturated alcohols having from 1 to about 5 carbon atoms such as methanol, ethanol, propanol, butanol and pentanol. The preferred aromatic alcohols are phenyl substituted, saturated aliphatic alcohols with the aliphatic moiety having from 1 to about 3 carbon atoms such as phenylmethanol, phenylethanol and phenylpropanol. The preferred organic acid accelerators and the metallic salts of such acids have from 2 to about 10 carbon atoms and include, for example, acetic acid, proprionic acid, caproic acid and zinc acetate.

The reaction rate activator is generally used in an amount from about 1 to about 30 wt.% and preferably in an amount from about 1 to about 20 wt.% based on the weight of the polycarboxylic acid, provided however, that the upper weight limit of the organic acids and the metallic salts of such acids does not exceed about 10 wt.% based on the weight of the polycarboxylic acid. A mixture containing a predominant amount of alcohol as, for example, 75 wt.% ethanol and a minor amount of organic acid as, for example, 25 wt.% acetic acid (or zinc acetate) is particularly suitable as an accelerator since the strong odor of the acid is masked resulting in an impression material which is more palatable to the dental patient. The concentration of the accelerator is so selected that the set time of the composition does not exceed about 15 minutes.

The hydrocarbon binding resin is advantageously included in the polycarboxylic acid component to improve adhesion, impart toughness and reduce brittleness of the interacted product. The hydrocarbon resin is generally added to the polycarboxylic acid component in an amount from about 0.3 to about 1.3 parts by weight per 1.0 part by weight of the polycarboxylic acid. Suitable hydrocarbon resins include polyterpene resins. Polyterpene resins consists essentially of polymers of alphaor beta-pinene having the empirical chemical formula $C_{10}H_{16}$ and are obtained by the polymerization of turpentine in the presence of catalysts such as aluminum chloride or mineral acids.

The addition to the formulation of water, as for example, to the polycarboxylic acid component in an amount from about 1 to about 5 wt.% based on the weight of the polycarboxylic acid further accelerates the rate of reaction between the acidic and basic components.

To facilitate handling in dental practice, the metallic base, a dry material, is blended into a suitable fluid carrier such as peanut oil, caster oil or mineral oil to impart flowerability to the base. The composition comprising the base is herein referred to as Component B. The composition comprising liquid polycarboxylic acid, accelerator and hydrocarbon resin is a flowable material which is herein referred to as Component A. In use, Component A and Component B are packaged in separate extrusion tubes and are so formulated that the dispensing of substantially equal amounts thereof provides a suitable concentration of ingredients for mixing and subsequent setting in oral application.

The compositions prepared by interacting the metallic base with the high molecular weight organic acid in the presence of an accelerator and a hydrocarbon resin are particularly well suited for use as dental impression material.

A pulp capping preparation is obtained by formulating the polycarboxylic acid component containing accelerator and hydrocarbon resin with about 1 to about 5 wt.% resin oil and about 0.5 to about 5 wt.% of ethyl cellulose based on the weight of the polycarboxylic acid and interacting this formulated component with the metallic base component.

A temporary cement is prepared by formulating the polycarboxylic acid component containing accelerator and hydrocarbon resin with a filler such as polymethylmethacrylate powder and interacting the same with the metallic base component.

By adding lanolin, resin oil and paraffin wax to the polycarboxylic acid component containing accelerator and hydrocarbon resin and interacting the same with the metallic base component, there is obtained a composition which is suitable for use as a periodontal pack.

EXAMPLES

The following examples further illustrate the invention.

$C_{36}$ dimer acid and $C_{54}$ trimer acid used in the examples are available from Emery Industries, Inc. under the trademarks EMPOL 1018 and EMPOL 1040, respectively. EMPOL 1018 contains 83% of $C_{36}$ dibasic acid (M.W. approx. 565), 17% of $C_{54}$ tribasic acid (M.W. approx. 845), and a trace of $C_{18}$ monobasic acid (M.W. approx. 282). EMPOL 1040 contains 20% of $C_{36}$ dibasic acid and 80% $C_{54}$ tribasic acid.

Polyterpene resin used in the examples is available under the trademark PICCOLYTE A from Hercules, Inc. of Wilmington, Del. This hydrocarbon resin is described as being derived from alpha-pinene and has the following properties and characteristics:

|  | Polyterpene Resin PICCOLYTE C115 |
| --- | --- |
| Softening point, R&B, °C. | 10 |
| Color, Gardner | 4 |
| Acid number | <1 |
| Saponification number | <1 |
| Bromine number | 17 |
| Iodine number | 35 |
| Specific gravity at 25° C. | 0.93 |
| Refractive index at 25° C. | 1.51 |
| Flash point, COC, °C. | 229 |

In examples I through III, the following procedure was employed.

Component A was prepared by mixing the polycarboxylic acid with the other ingredients at moderately elevated temperatures, where required, to obtain a flowable mixture.

Component B was prepared by mechanically mixing the metallic base with the fluid carrier at room temperature until a smooth mixture was obtained.

Extrusion tubes were filled with Component A and with Component B. Equal amounts of Components A and B were dispensed onto a mixing board at room temperature and hand mixed. The time that it took the mixture to form a solid, cementitious, coherent mass is set forth in each example as set time in minutes.

EXAMPLE I

| Component A | Set time: 5 minutes Wt. grams | Component B | wt. grams |
| --- | --- | --- | --- |
| $C_{36}$ dimer acid | 30 | Zinc oxide | 60 |
| Polyterpene resin | 20 | Magnesium oxide | 30 |
| Ethanol | 0.5 | Peanut oil | 10 |

EXAMPLE II

| Component A | wt. grams | Set time: 4 minutes<br>Component B | wt. grams |
|---|---|---|---|
| $C_{54}$ trimer acid | 30 | Zinc oxide | 60 |
| Polyterpene resin | 19 | Magnesium oxide | 30 |
| Phenylmethanol | 1 | Peanut oil | 10 |

EXAMPLE III

| Component A | wt. grams | Set time: 4 minutes<br>Component B | wt. grams |
|---|---|---|---|
| $C_{36}$ dimer acid | 100 | Magnesium oxide | 90 |
| Isopropanol | 1.5 | Peanut oil | 10 |
| Ethanol | 1 | | |

EXAMPLE IV

This example illustrates the concentration range for the alcohol activators used in the preparation of the settable compositions. The compositions were prepared by direct hand mixing of the ingredients at room temperature and set times were noted. The term "dimer acid" in the examples refers to $C_{36}$ dimer acid and the term "trimer acid" in the examples refers to $C_{54}$ trimer acid.

| Ingredients | wt. grams | Set time Minutes |
|---|---|---|
| Example 4(a) | | 160 |
| Dimer acid | 40 | |
| Zinc oxide | 60 | |
| Example 4(b) | | 105 |
| Dimer acid | 39 | |
| Zinc oxide | 60 | |
| Ethanol | 1 | |
| Example 4(c) | | 12 |
| Dimer acid | 35 | |
| Zinc oxide | 55 | |
| Ethanol | 10 | |
| Example 4(d) | | 30 |
| Dimer acid | 39 | |
| Zinc oxide | 60 | |
| Phenylmethanol | 1 | |
| Example 4(e) | | 9 |
| Dimer acid | 39 | |
| Zinc oxide | 59 | |
| Phenylmethanol | 1 | |
| Water | 1 | |
| Example 4(f) | | 67 |
| Dimer acid | 39 | |
| Zinc oxide | 60 | |
| Isopropanol | 1 | |
| Example 4(g) | | 50 |
| Dimer acid | 40 | |
| Magnesium oxide | 60 | |
| Example 4(h) | | 10 |
| Dimer acid | 39 | |
| Magnesium oxide | 60 | |
| Ethanol | 1 | |
| Example 4(i) | | 6 |
| Dimer acid | 35 | |
| Magnesium oxide | 55 | |
| Ethanol | 10 | |
| Example 4(j) | | 8 |
| Dimer acid | 39 | |
| Magnesium oxide | 60 | |
| Phenylmethanol | 1 | |
| Example 4(k) | | 5 |
| Dimer acid | 39 | |
| Magnesium oxide | 59 | |
| Ethanol | 1 | |
| Water | 1 | |
| Example 4(l) | | 15 |
| Dimer acid | 39 | |
| Zinc oxide | 30 | |
| Magnesium oxide | 30 | |
| Ethanol | 1 | |
| Example 4(m) | | 160 |
| Trimer acid | 40 | |
| Zinc oxide | 60 | |
| Example 4(n) | | 115 |
| Trimer acid | 39 | |
| Zinc oxide | 60 | |
| Ethanol | 1 | |
| Example 4(o) | | 6 |
| Trimer acid | 35 | |
| Magnesium oxide | 55 | |
| Isopropanol | 10 | |

EXAMPLE V

This example illustrates the use of acid accelerators and hydrocarbon binding resins in the preparation of settable dental compositions based on the interaction of a polycarboxylic acid with a metallic base and also illustrates the effect of added water on set time. The compositions were prepared by direct hand mixing of the ingredients at room temperature and set times were noted. In the procedure followed, three grams of dry zinc oxide were added to and mixed with five gram samples of the polycarboxylic acid component with the latter originally being prepared in 100 gram quantities. The term "dimer acid" in the examples refers to $C_{36}$ dimer acid.

| Ingredients | wt. grams | Set time Minutes |
|---|---|---|
| Example 5(a) | | 5 |
| Dimer acid | 3.35 | |
| Polyterpene resin | 1.50 | |
| Acetic acid | 0.15 | |
| Zinc oxide | 3.00 | |
| Example 5(b) | | 4.5 |
| Dimer acid | 3.35 | |
| Polyterpene resin | 1.50 | |
| Acetic acid | 0.10 | |
| Water | 0.05 | |
| Zinc oxide | 3.00 | |
| Example 5(c) | | 35 |
| Dimer acid | 3.25 | |
| Polyterpene resin | 1.50 | |
| Water | 0.25 | |
| Zinc oxide | 3.00 | |
| Example 5(d) | | 3 |
| Dimer acid | 3.25 | |
| Polyterpene resin | 1.50 | |
| Acetic acid | 0.25 | |
| Zinc oxide | 3.00 | |
| Example 5(e) | | 6 |
| Dimer acid | 3.25 | |
| Polyterpene resin | 1.50 | |
| Zinc acetate | 0.15 | |
| Water | 0.10 | |
| Zinc oxide | 3.00 | |
| Example 5(f) | | 3.5 |
| Dimer acid | 3.05 | |
| Polyterpene resin | 1.50 | |
| Zinc acetate | 0.25 | |
| Water | 0.20 | |
| Zinc oxide | 3.00 | |
| Example 5(g) | | 3<br>(material brittle) |
| Dimer acid | 4.75 | |
| Acetic acid | 0.25 | |

| Ingredients | wt. grams | Set time Minutes |
|---|---|---|
| Zinc oxide | 3.00 | |

In view of the foregoing description and examples, it will become apparent to those of ordinary skill in the art that equivalent modifications thereof may be made without departing from the spirit and scope of this invention.

That which is claimed is:

1. A method for preparing an oral, settable dental composition which comprises interacting:
   component A containing:
   (i) a polycarboxylic acid selected from the group consisting of $C_{36}$ dimer acid, $C_{54}$ trimer acid and mixtures thereof,
   (ii) a reaction rate activator selected from the group consisting of lower aliphatic alcohols, lower aromatic alcohols, lower aliphatic organic acids, calcium, magnesium and zinc salts of said acids, and mixtures thereof, said reaction rate activator being present in an amount from about 1 to about 30 wt.% based on the weight of the polycarboxylic acid, provided however, that the upper weight limit of the lower aliphatic organic acids and the calcium, magnesium and zinc salts of said acids does not exceed about 10 wt.% based on the weight of the polycarboxylic acid, and
   (iii) polyterpene resin in an amount from about 0.3 to about 1.3 parts by weight per 1.0 part by weight of polycarboxylic acid; and
   component B containing a metallic base selected from the group consisting of oxides and hydroxides of zinc, magnesium, calcium, copper and mixtures thereof, said metallic base being present in an amount from about 0.1 to about 4.0 parts by weight per 1.0 part by weight of polycarboxylic acid.

2. The method of claim 1 wherein the reaction rate activator is present in Component A in an amount from about 1 to about 20 wt.% based on the weight of the polycarboxylic acid.

3. The method of claim 1 wherein the lower aliphatic alcohol is a saturated aliphatic alcohol having from 1 to about 5 carbon atoms.

4. The method of claim 3 wherein the alcohol is ethanol.

5. The method of claim 1 wherein the lower aromatic alcohol is a phenyl substituted, saturated aliphatic alcohol with the aliphatic moiety having from 1 to about 3 carbon atoms.

6. The method of claim 5 wherein the alcohol is phenylmethanol.

7. The method of claim 1 wherein the lower aliphatic organic acid has from about 2 to about 10 carbon atoms.

8. The method of claim 7 wherein the acid is acetic acid.

9. The method of claim 1 wherein the reaction rate activator is a mixture of acetic acid and ethanol.

10. The method of claim 1 wherein the polycarboxylic acid is $C_{36}$ dimer acid.

11. The method of claim 1 wherein the polycarboxylic acid is $C_{54}$ trimer acid.

12. The method of claim 1 wherein the metallic base is zinc oxide.

13. The method of claim 1 wherein the metallic base is a mixture of zinc oxide and magnesium oxide.

14. The method of claim 1 wherein the metallic base is present in an amount from about 0.25 to about 3.0 parts by weight per 1.0 part by weight of polycarboxylic acid.

15. A solid, coherent, cementitious, dental composition prepared by interacting:
   component A containing:
   (i) a polycarboxylic acid selected from the group consisting of $C_{36}$ dimer acid, $C_{54}$ trimer acid and mixtures thereof,
   (ii) a reaction rate activator selected from the group consisting of lower aliphatic alcohols, lower aromatic alcohols, lower aliphatic organic acids, calcium, magnesium and zinc salts of said acids, and mixtures thereof, said reaction rate activator being present in an amount from about 1 to about 30 wt.% based on the weight of the polycarboxylic acid, provided however, that the upper weight limit of the lower aliphatic organic acids and the calcium, magnesium and zinc salts of said acids does not exceed about 10 wt.% based on the weight of the polycarboxylic acid, and
   (iii) polyterpene resin in an amount from about 0.3 to about 1.3 parts by weight per 1.0 part by weight of polycarboxylic acid; and
   component B containing a metallic base selected from the group consisting of oxides and hydroxides of zinc, magnesium, calcium, copper and mixtures thereof, said metallic base being present in an amount from about 0.1 to about 4.0 parts by weight per 1.0 part by weight of polycarboxylic acid.

16. A two-component system interactable to form an oral, settable dental composition comprising:
   component A containing:
   (i) a polycarboxylic acid selected from the group consisting of $C_{36}$ dimer acid, $C_{54}$ trimer acid and mixtures thereof,
   (ii) a reaction rate activator selected from the group consisting of lower aliphatic alcohols, lower aromatic alcohols, lower aliphatic organic acids, calcium, magnesium and zinc salts of said acids, and mixtures thereof, said reaction rate activator being present in an amount from about 1 to about 30 wt.% based on the weight of the polycarboxylic acid, provided however, that the upper weight limit of the lower aliphatic organic acids and the calcium, magnesium and zinc salts of said acids does not exceed about 10 wt.% based on the weight of the polycarboxylic acid, and
   (iii) polyterpene resin in an amount from about 0.3 to about 1.3 parts by weight per 1.0 part by weight of polycarboxylic acid; and
   component B containing a metallic base selected from the group consisting of oxides and hydroxides of zinc, magnesium, calcium, copper and mixtures thereof, said metallic base being present in an amount from about 0.1 to about 4.0 parts by weight per 1.0 part by weight of polycarboxylic acid.

* * * * *